(12) United States Patent
Yamazaki et al.

(10) Patent No.: US 6,496,735 B1
(45) Date of Patent: Dec. 17, 2002

(54) PORTABLE PULSE SHAPE-UP APPARATUS

(75) Inventors: Iwao Yamazaki; Yoshihiro Izawa, both of Tokyo (JP)

(73) Assignee: Ya-Man Ltd., Tokyo (JP)

( * ) Notice: Subject to any disclaimer, the term of this patent is extended or adjusted under 35 U.S.C. 154(b) by 0 days.

(21) Appl. No.: 09/509,527

(22) PCT Filed: Oct. 6, 1998

(86) PCT No.: PCT/JP98/04511

§ 371 (c)(1),
(2), (4) Date: Mar. 31, 2000

(87) PCT Pub. No.: WO99/17838

PCT Pub. Date: Apr. 15, 1999

(30) Foreign Application Priority Data

Oct. 6, 1997 (JP) .............................. 9-289065
Oct. 6, 1997 (JP) .............................. 9-289066

(51) Int. Cl.⁷ ................................................. A61N 1/08
(52) U.S. Cl. ....................................................... 607/72
(58) Field of Search ................................ 607/152, 149, 607/115, 72–74; 604/20

(56) References Cited

U.S. PATENT DOCUMENTS 2,667,162 A  *  1/1954  Zwahlen
6,151,528 A  *  11/2000  Maida

* cited by examiner

*Primary Examiner*—Mark Bockelman
(74) *Attorney, Agent, or Firm*—Jones, Tullar & Cooper, P.C.

(57) ABSTRACT

A portable pulse beauty treatment apparatus according to the present invention permits one to move freely while taking a desired pulse beauty treatment, thus making it unnecessary to allot a relatively long time of period exclusively to the pulse beauty treatment. A belt bag contains a control box having a pulse generator installed therein for effecting a pulse beauty treatment, and one wears the belt bag round one's waist. An electroded union suit has bundles of wires connecting its flat electrodes to the pulse generator in the control box, thus permitting the pulse generator to supply the flat electrodes with a train of pulses via the bundles of electric wires. The control box has two pairs of electrodes provided on its opposite sides for measurement of body impedance.

1 Claim, 7 Drawing Sheets

PORTABLE PULSE SHAPE-UP APPARATUS

TECHNICAL FIELD

The present invention relates to a pulse beauty treatment apparatus whose electric pulse supply applies a train of electric voltage pulses to selected portions of the body with the aid of electrodes, thereby electrically stimulating the body for beauty treatment.

BACKGROUND ART

Bioelectric current is flowing ceaselessly in the body to assist cells with their activities and muscles with their constriction.

The pulse beauty treatment apparatus can supply a train of current pulses to the body for stimulation, thereby activating cells even more and muscular contraction for improving the function of the body as the bioelectric current would do in flowing in the body. Particularly the pulse treatment has the effect of sliming one's body.

A conventional pulse beauty treatment apparatus has a plurality of flat electrodes connected to its stationary pulse equipment. Specifically these flat electrodes are arranged at selected positions on an associated mat, and one lies down on the mat with one's back or front upside, thereby permitting pulse current to flow in the body.

The practice of pulse beauty treatment, however, restrains one from assuming one's postures other than lying down on the electroded mat, not permitting one to move, walk or work. Inconveniently one cannot, therefore, take such a beauty treatment unless time permits.

What the present invention aims at is to permit one to move freely while taking a beauty treatment, thus permitting one to make full use of time involved for beauty treatment to perform other useful activities.

SUMMARY OF THE INVENTION

A portable pulse beauty treatment apparatus according to the present invention comprises:

a control box including a console and a pulse generator for providing a train of controlled pulses, thereby effecting a desired pulse beauty treatment;

connecting means for applying the train of controlled pulses to electrodes, which are applied to the inner surface of a garment made of stretch cloth; and wearing means for permitting one to have the control box on one's body whereby a desired beauty treatment may be effected when one has the electrodes and the control box on one's body.

The control box further has two pairs of terminal electrodes electrically isolated and attached to its outer surface, thereby permitting the measuring of the body impedance when one's hands are put on the four terminal electrodes. Connecting means for applying the train of controlled pulses to electrodes, which are adapted to be applied to the body; and wearing means for permitting one to have the control box on one's body, whereby a desired beauty treatment may be effected when one has the electrodes and the control box on one's body.

DETAILED DESCRIPTION OF THE PREFERRED EMBODIMENTS

Figure 1:
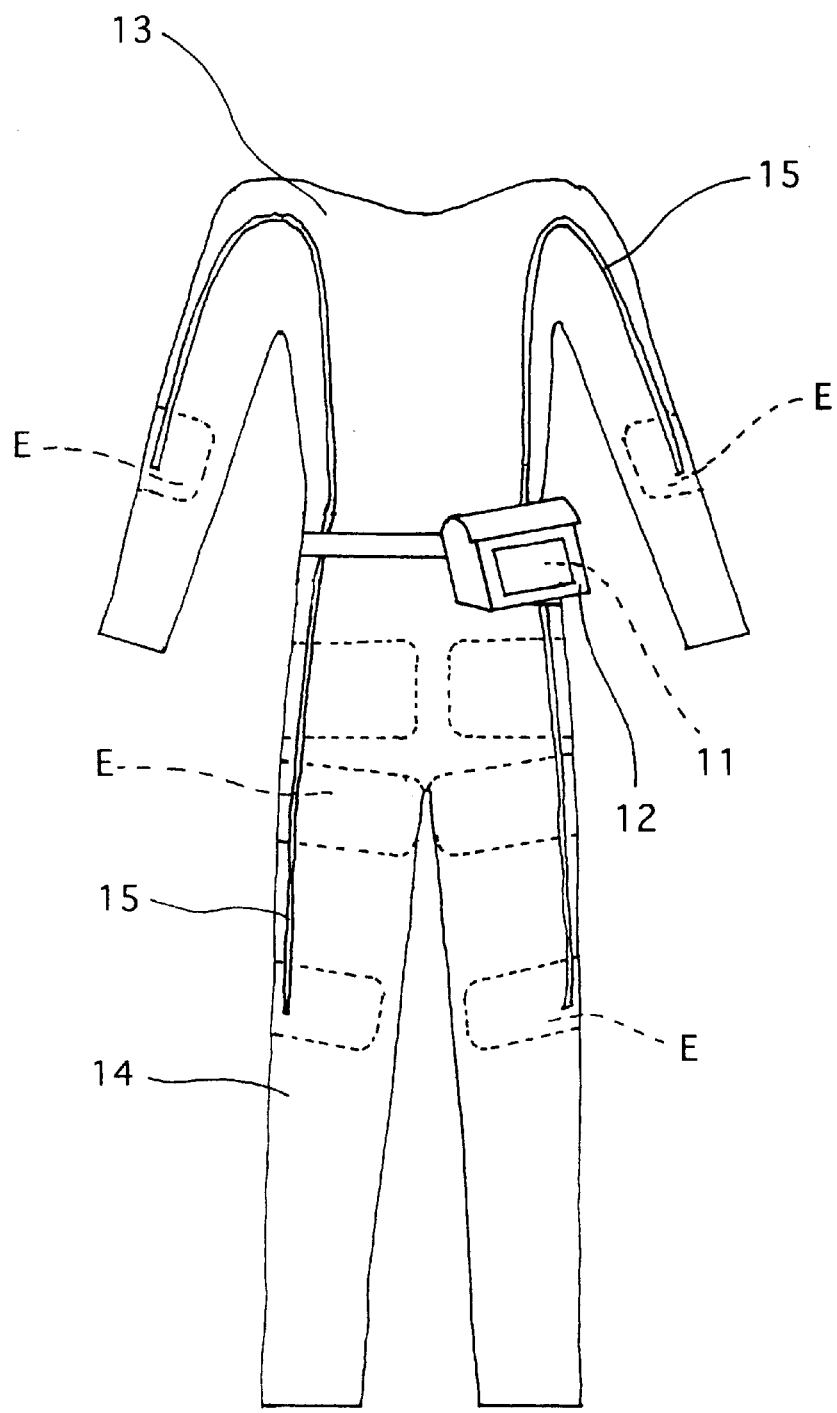
FIG. 1 illustrates that one wears a portable pulse beauty treatment apparatus according to one embodiment of the present invention.

Referring to FIG. 1, a portable pulse beauty treatment apparatus according to one preferred embodiment of the present invention is worn on one's body, particularly round one's waist. It comprises a control box having a pulse generator and a body impedance measuring circuit incorporated therein, thus permitting estimation of one's body impedance and practice of beauty treatment. One wears a union suit or a jacket 13 and a pair of tights 14 having a plurality of electrodes attached inside at selected parts. The control box 11a is put in the belt bag 12 to be worn round one's waist.

The control box 11 supplies the electrodes E with pulses via bundles of electric wires 15.

Figure 2:
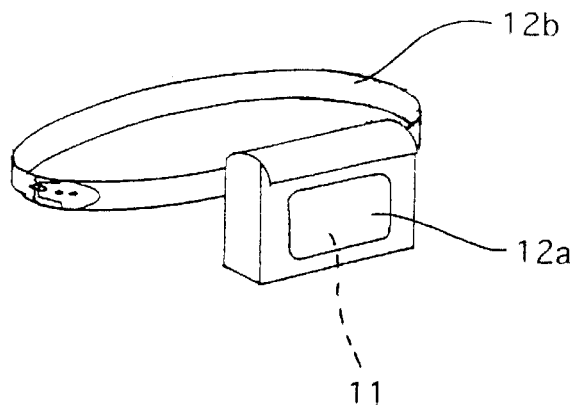
FIG. 2 illustrates a belt bag-like pulse treatment apparatus.
Figure 3:
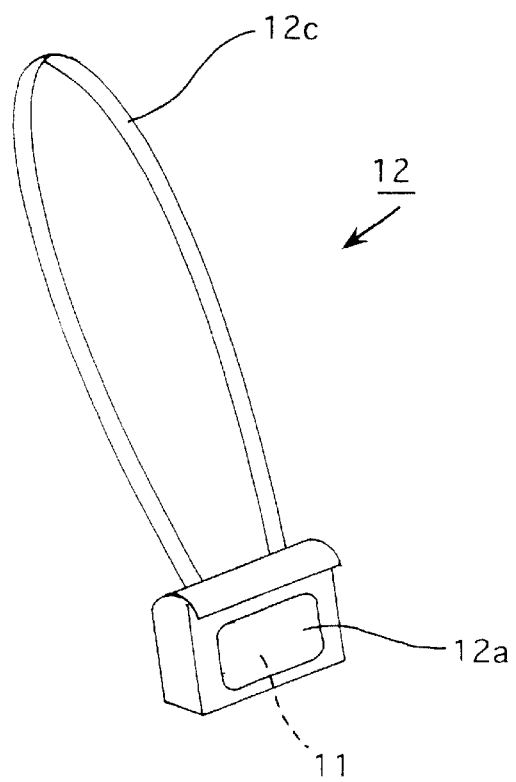
FIG. 3 illustrates a shoulder bag-like pulse treatment apparatus.

As seen from FIG. 2, the belt bag 12 contains the control box 11, and it has a rectangular transparency 12a on its front, thereby permitting the controlling of the console of the control box 11. The belt bag 12 has a belt 12b fixed to its rear side. FIG. 3 shows a shoulder bag-like beauty treatment apparatus, to which a shoulder strap 12c is fixed to make it easy to carry by hanging the bag from the shoulder.

A union suit is made of a stretch cloth, and it has a plurality of flat electrodes E applied to its inside, thus permitting these electrods E to be applied to selected parts of the body when one wears the union suit.

The electroded union suit has the male (or female) parts of press studs (not shown) fixed to its outside, the male parts being electrically connected to the electrodes E. On the other hand, the female (or male) parts of the press studs are fixed to the ends of the electric wires 15, thus permitting the electric wires 1 to be connected to the flat electrodes E by snapping the male parts in the female parts of the press studs.

Figure 4:
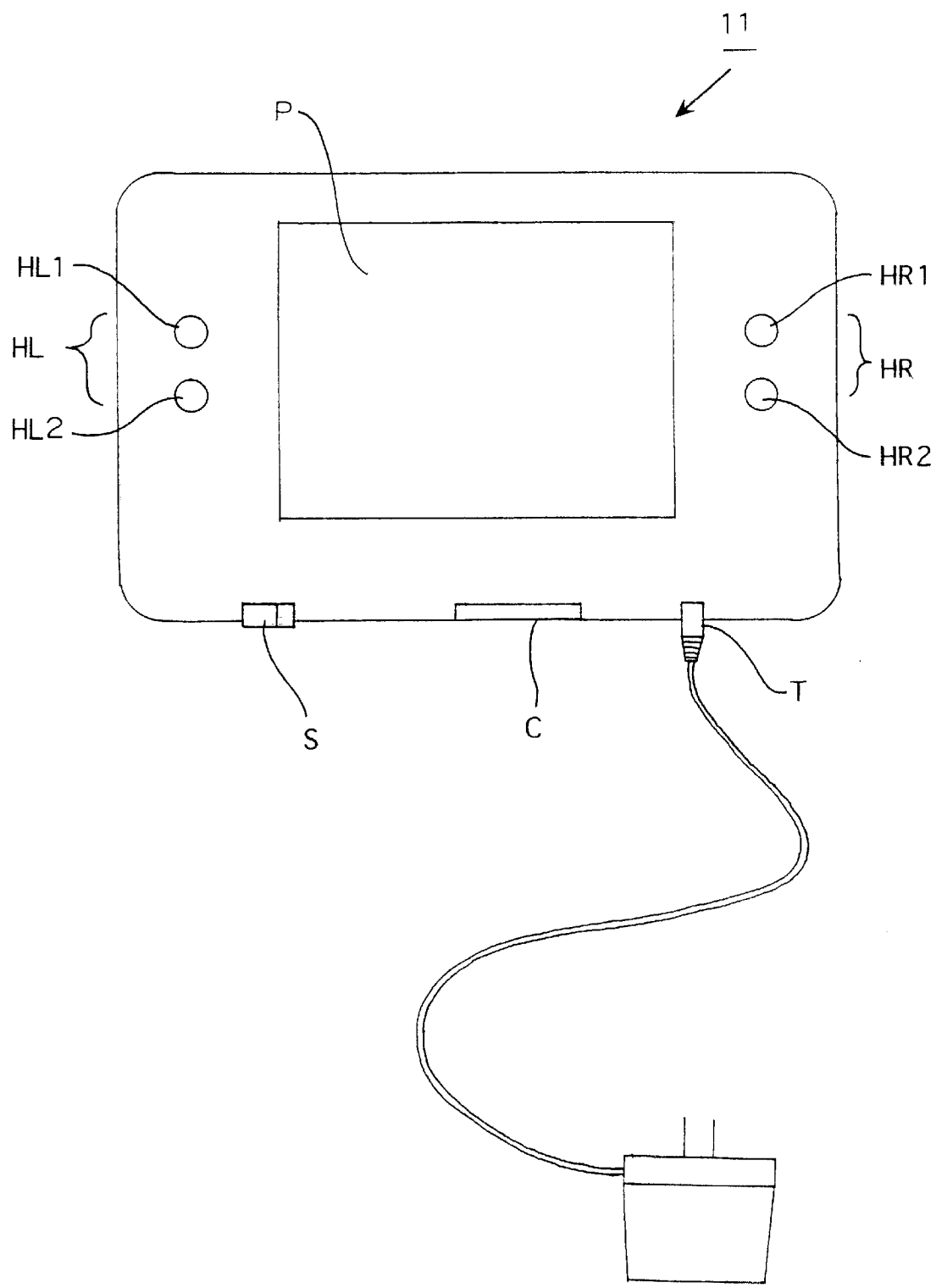
FIG. 4 is a front view of the control box.

As seen from FIG. 4, the control box 11 has a touch-sensitive color liquid crystal panel P on its front side, and two insulating grip sections HL and HR formed on its opposite sides.

On the lower side of the control box attached are a power switch S, a connector C of the bundles of electric wires 15 and a terminal T for an exterior power supply.

A color liquid panel which is responsive to associated key switches can be used in place of the touch-sensitive panel P.

A battery may be installed in the control box 11, so that the terminal T for an exterior power supply may be omitted.

The opposite grip sections HL and HR have upper feeding terminals HL1 and HR1 and lower detecting terminals HL2 and HR2.

These feeding and detecting terminals are plated with hard chrome, and are connected to a body impedance measuring circuit within the housing.

Figure 5:
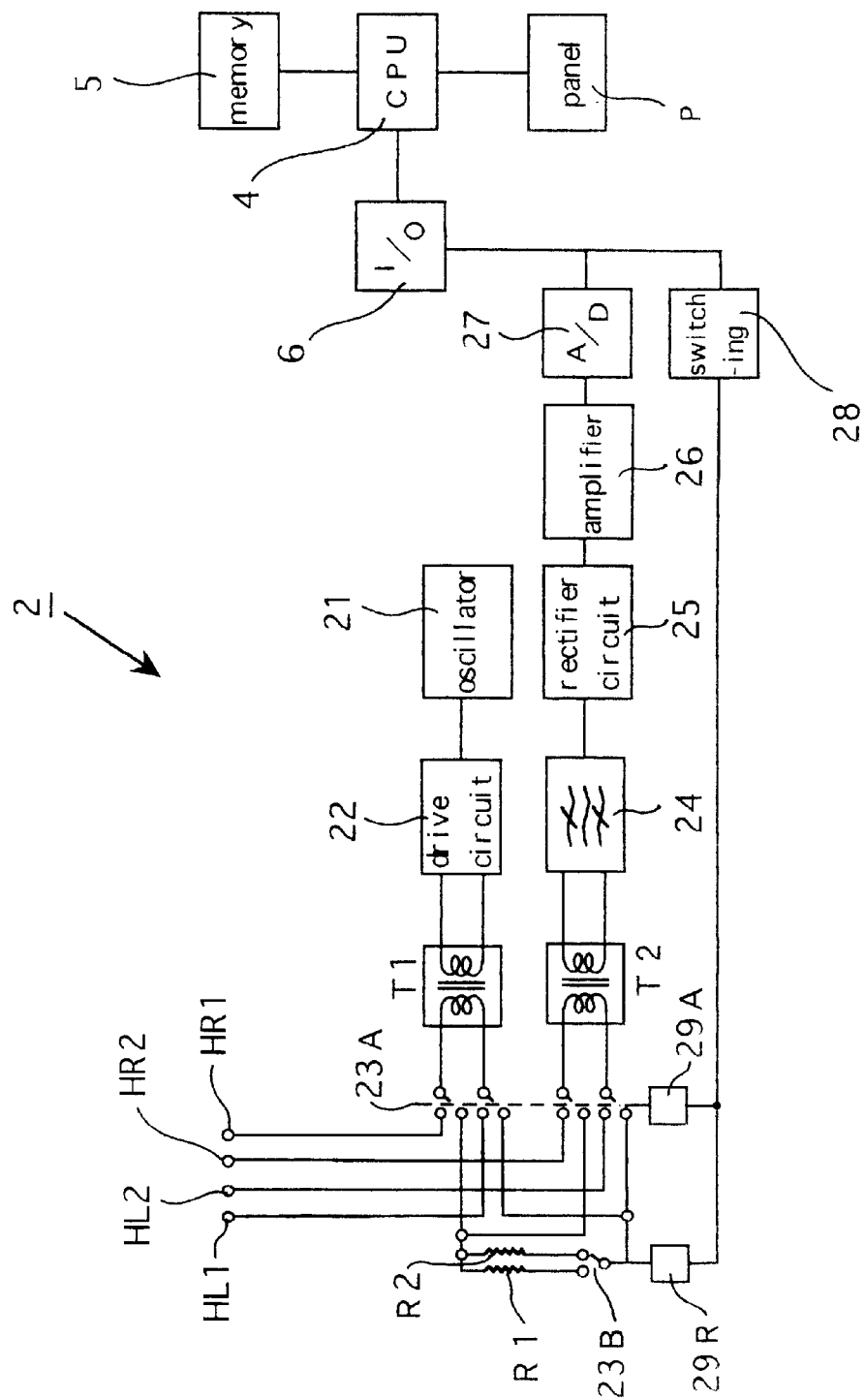
FIG. 5 is a block diagram showing a body impedance measuring circuit.

Referring to FIG. 5, the body impedance measuring circuit 2 works as follows: an oscillator 21 applies sinusoidal ac voltage of 50 kHz to the feeding terminals HL1 and HR1 via an associated drive circuit 22, a transformer T1 and a switching means 23A.

Figure 6:
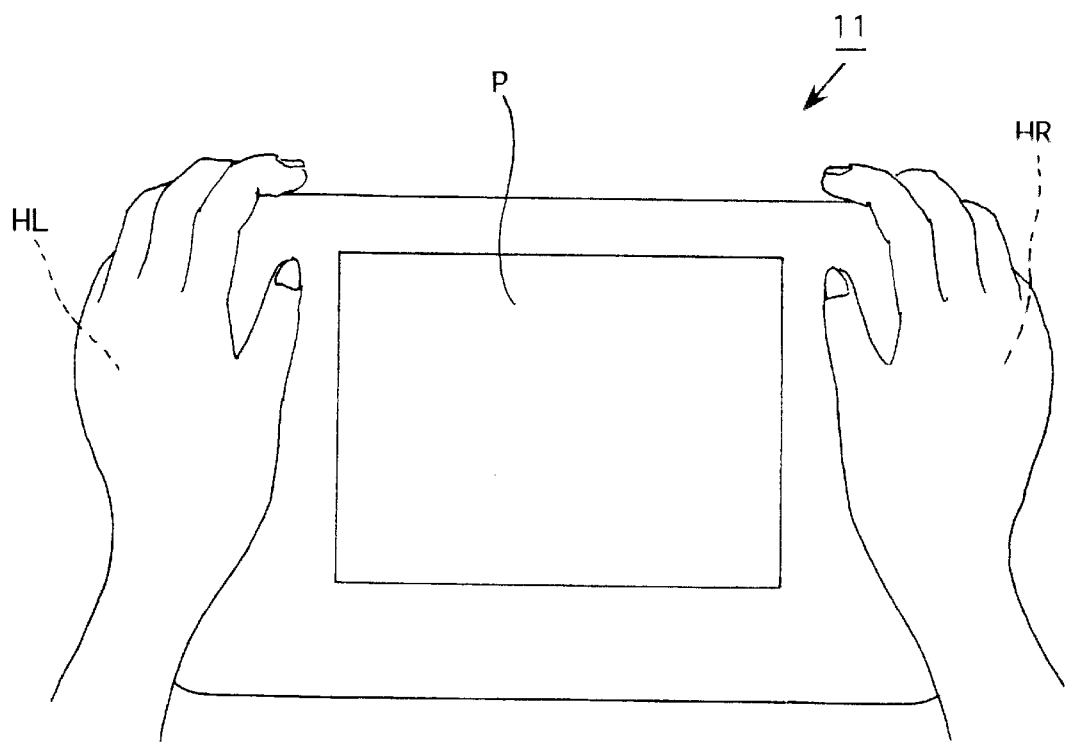
FIG. 6 illustrates how the body impedance can be measured.

Referring to FIG. 6, one's left and right hands are put on the opposite grip sections HL and HR, allowing their palms to be put in contact with the feeding terminals HL1 and HR1 and the detecting terminals HL2 and HR2 simultaneously.

Figure 8:
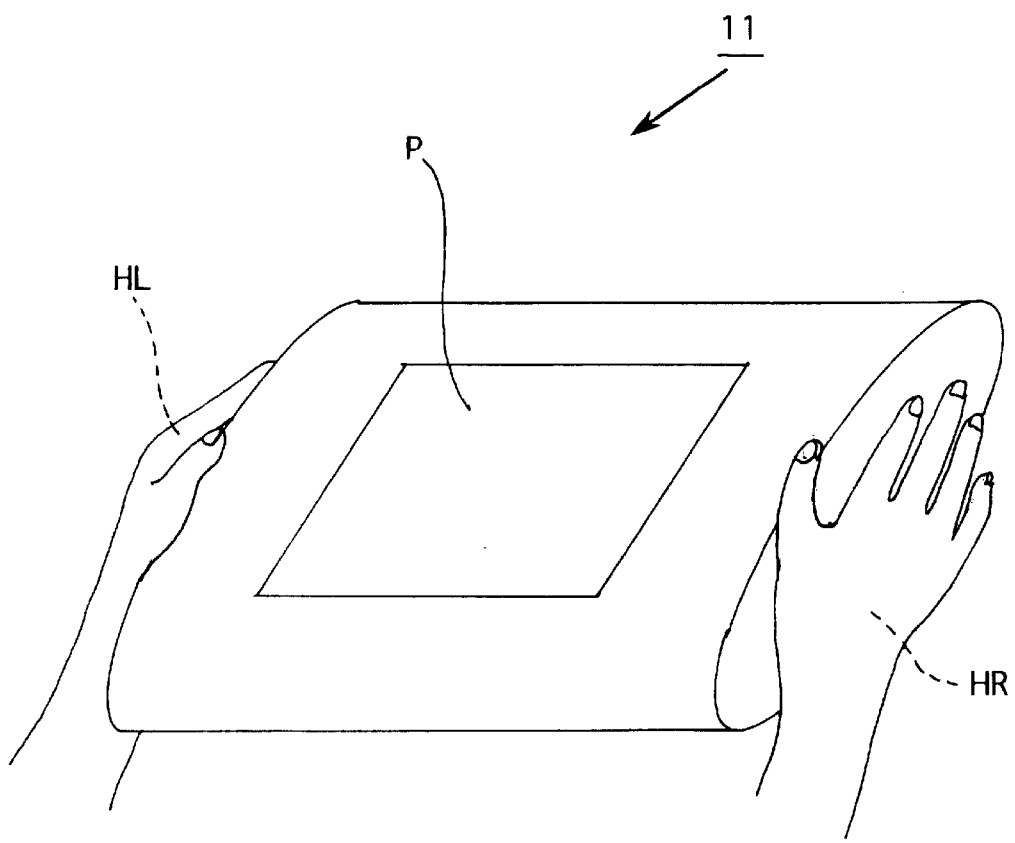
FIG. 8 illustrates how the body impedance can be measured in a different way from FIG. 6.

Referring to FIG. 8, one's left and right hands are put on the opposite sides of the control box 11; the grip sections HL and HR are formed on the opposite sides of the control box 11.

Then, the ac voltage is applied to the feeding terminals HL1 and HR1 so that the ac current flows from one to the other hand through the body to cause an ac voltage to appear between the detecting terminals HL2 and HR2.

The ac voltage appearing between the detecting terminals HL2 and HR2 is converted to the corresponding dc voltage after passing through the switching means 23A, a transformer T2, a band-pass filter 24, a rectifier circuit 25 and an amplifier 26. The so converted dc voltage is reshaped, level-adjusted and offset-adjusted to be applied to a CPU4 via an A/D converter 27 and an I/O interface 6. Thus, the CPU4 determines the body impedance and the body fat rate from the body impedance to show the body fat rate on the color liquid crystal panel P.

The detecting part of the body impedance measuring circuit 2 is preferably calibrated in its input versus output characteristics before measuring the body impedance, thereby reducing any errors which otherwise, would be caused by the age-variation and temperature-dependent variation of circuit elements.

As for the callibration two variables of known values, that is, the body impedance Z and the voltage V appearing at the detecting terminals are put in the following equation, which represents a regression curve: $Z=kV+C0$.

Specifically two resistors R1 and R2 of known values are connected one after another between the feeding terminals on the opposite sides of the control box 11 in place of the body impedance Z, and then a predetermined ac voltage, which is used in determining the body impedance Z, is applied across each resistor to determine the voltage appearing thereacross, so that the constants k and C0 in the equation are determined.

More specifically the CPU 4 directs a control signal to the switching means 23 A via the I/O interface 6, a switching unit 28 and a switching control 29A so that one of the two resistors R1 and R2 are put in circuit with the secondary winding of the transformer T1 and the primary winding of the transformer T2 for measuring the voltage appearing across the so selected resistor R1 or R2. Then, the CPU 4 directs another control signal to the switching means 23 B via the I/O interface 6, the switching unit 28 and a switching control 29B so that the other resistor R1 or R2 are selected for measurement.

Figure 7:
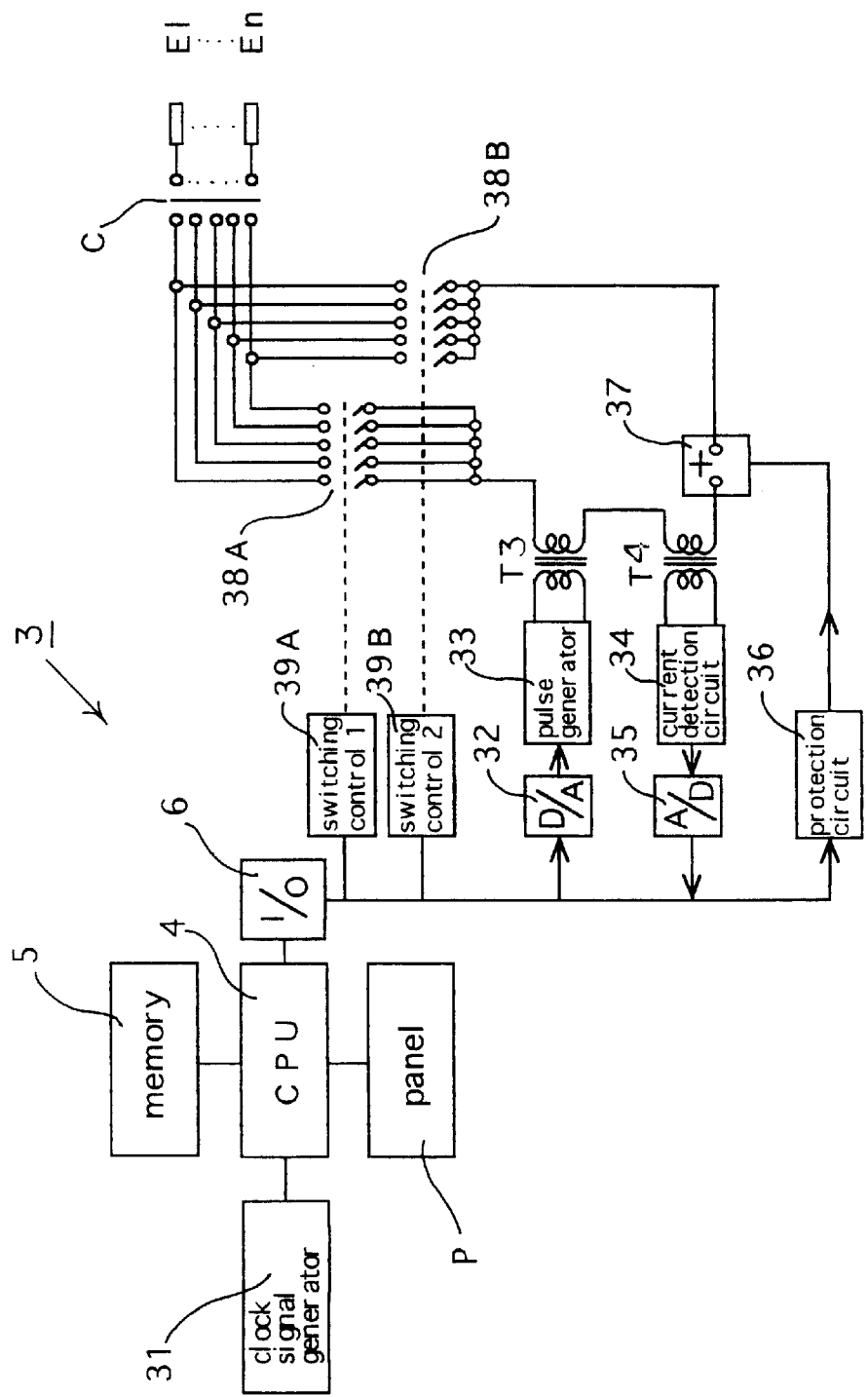
FIG. 7 is a block diagram showing a pulse generator system.

FIG. 7 shows a pulse generator system 3. It comprises a color liquid crystal panel P, a CPU 4, a memory 5, a clock signal generator 31, an interface 6, a digital-to-analog converter 32, a pulse generator 33, a current detector 34, an analog-to-digital converter 35, a protection circuit 36, a breaker 37, and switching circuits 38A and 38B. A desired kind of beauty treatment and a desired pulse-application pattern are selectively read from the memory 5 with the aid of the CPU 4, and the reference clock signal generator 31 is so controlled that the clock pulses may be divided to provide digital trigger signals to meet the demand. The trigger signals are directed to the pulse generator 33 via the interface 6 and the D/A converter 32, thus permitting the pulse generator 33 to produce pulses of predetermined width and recurrence, which are directed to the primary winding of an associated transformer T3.

The current detector 34 is connected to another transformer T4 parallel-connected to the transformer T3, thereby watching and making a decision as to whether or not an excessive current is flowing.

The electric current thus detected is directed to the CPU 4 via the A/D converter 35 and the I/D interface 6, so that the CPU4 may permit the protection circuit 36 to respond to the rise of the electric current beyond the threshold value for actuating the breaker 37.

The switching circuits 38A and 38B are connected to the series-connection of the secondary windings of the transformers T3 and T4. The flat electrodes E1 to En are connected to the switching circuits 38A and 38B via the connector C.

The switching circuits 38A and 38B are so designed as to perform their switching actions via associated photocouplers, which are responsive to signals from associated selectors 39A and 39B for making electric connections between the pulse generator 33 and flat electrodes selected among those E1 to En.

Thus, the flat electrodes E1 to En are selectively combined to allow pulse current to flow in the so selected flat electrodes in such a pulse-application pattern that the desired beauty treatment may be effected on the body.

More specifically, one contact is selected among the contacts each of the switching circuits 38A and 38B, and the two contacts thus selected are closed to provide two closed circuits including two flat electrodes associated with the selected and closed contacts and the selected portions of the body facing the two flat electrodes. Thus, the selected portions of the body are stimulated by pulses from the pulse generator 33 for beauty treatment.

One kind of beauty treatment is called "toning", which can be carried out by applying pulses at a relatively low recurrence ranging from 5 to 10 Hz, thereby giving stimulation to a deep point in the body to cause the skeletal muscle movement, thereby expediting the blood circulation and kneading the selected portion of the body. Another kind of beauty treatment is called "drainage", which can be carried out by applying pulses at a relatively high recurrence ranging from 20 to 100 Hz, thereby giving stimulation to a shallow point in the body to cause the muscle movement under the skin, thereby expediting the flow of lymph in the body and reducing dropsies, if any.

Special "toning" or "drainage" uses up-and-down cyclic variation of pulse voltage, thereby giving cyclic variable stimulation to the body.

In the ordinary "toning" or "drainage" pulse current is allowed to flow in all of the electrodes simultaneously. In the time-sequential "toning" or time-sequential "drainage" pulse current is allowed to flow in groups of electrodes one after another, and in the time-divisional "toning" or time-divisional "drainage", pulse current is allowed to flow in some selected groups of electrodes simultaneously.

The portable pulse beauty treatment apparatus according to the present invention permits one to take a beauty treatment by wearing an electroded union suit, which has a plurality of flat electrodes attached inside. The beauty treatment, therefore, does not require that one is naked to lie down, permitting any way of holding one's body. Thus, one is permitted to stand, sit in a chair, walk, work or take an exercise while taking a desired beauty treatment. The very close fitting of the stretch union suit assures that the electrodes are applied closely to the selected parts of the body. Also the tightening of the body by the close fitting of the stretch union suit is effectively combined with the expediting of the lymph flow and blood circulation by pulsating current, thus making it possible to reduce dropsies, if any.

The portable pulse beauty treatment apparatus according to the present invention permits one to determine one's body impedance simply by putting one's hands on the paired electrodes of the opposite grip sections, so that the body fat rate may be given on the liquid crystal display.

Thus, measurement of the body impedance and hence, the body fat rate is facilitated, requiring that no separate electrodes be applied to selected areas of the body, and therefore, the slimming effect can be realized while taking a beauty treatment.

The console can be handled by touching with fingers while holding the control box with hands, not requiring that one or the other hand be put apart from the control box to handle the console, and therefore, the handling of the console can be conveniently effected.

Electrode arrangement causes no offensive sight, and the pulse beauty treatment apparatus has a pleasing appearance.

What is claimed is:

1. A portable pulse beauty treatment apparatus characterized in that it comprises:

a control box including a console and a pulse generator for providing a train of controlled pulses, thereby effecting a desired pulse beauty treatment, the control box further having two pairs of terminal electrodes electrically isolated and attached to its outer surface, thereby permitting the measuring of the body impedance when one's hands are put on the four terminal electrodes;

connecting means for applying the train of controlled pulses to electrodes, which are adapted to be applied to the body; and wearing means for permitting one to have the control box on one's body, whereby a desired beauty treatment may be effected when one has the electrodes and the control box on one's body.

* * * * *